US00PP35082P2

(12) United States Plant Patent
Ranney et al.

(10) Patent No.: US PP35,082 P2
(45) Date of Patent: Apr. 4, 2023

(54) ***RHODODENDRON* PLANT NAMED 'NCRX11'**

(50) Latin Name: ***Rhododendron* hybrid**
Varietal Denomination: NCRX11

(71) Applicant: North Carolina State University, Raleigh, NC (US)

(72) Inventors: Thomas Green Ranney, Arden, NC (US); Darren H. Touchell, Arden, NC (US); Andra Windorf Nus, Arden, NC (US); Irene Palmer, Arden, NC (US); Nathan Lynch, Arden, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 17/845,517

(22) Filed: Jun. 21, 2022

(51) Int. Cl.
*A01H 5/00* (2018.01)
*A01H 6/36* (2018.01)

(52) U.S. Cl.
USPC ..... Plt./238

(58) Field of Classification Search
USPC ..... Plt./227, 238
See application file for complete search history.

(56) References Cited

U.S. PATENT DOCUMENTS

PP32,819 P2 * 2/2021 Ranney ..... A01H 5/02
Plt./239

* cited by examiner

*Primary Examiner* — Karen M Redden
(74) *Attorney, Agent, or Firm* — Cassandra Bright

(57) ABSTRACT

A new and distinct cultivar of *Rhododendron* plant named 'NCRX11' is disclosed, characterized by a prostrate, dwarf habit, and pink double flowers in spring that rebloom in early fall. The new cultivar is a *Rhododendron*, suitable for ornamental garden purposes.

2 Drawing Sheets

Figure 1:
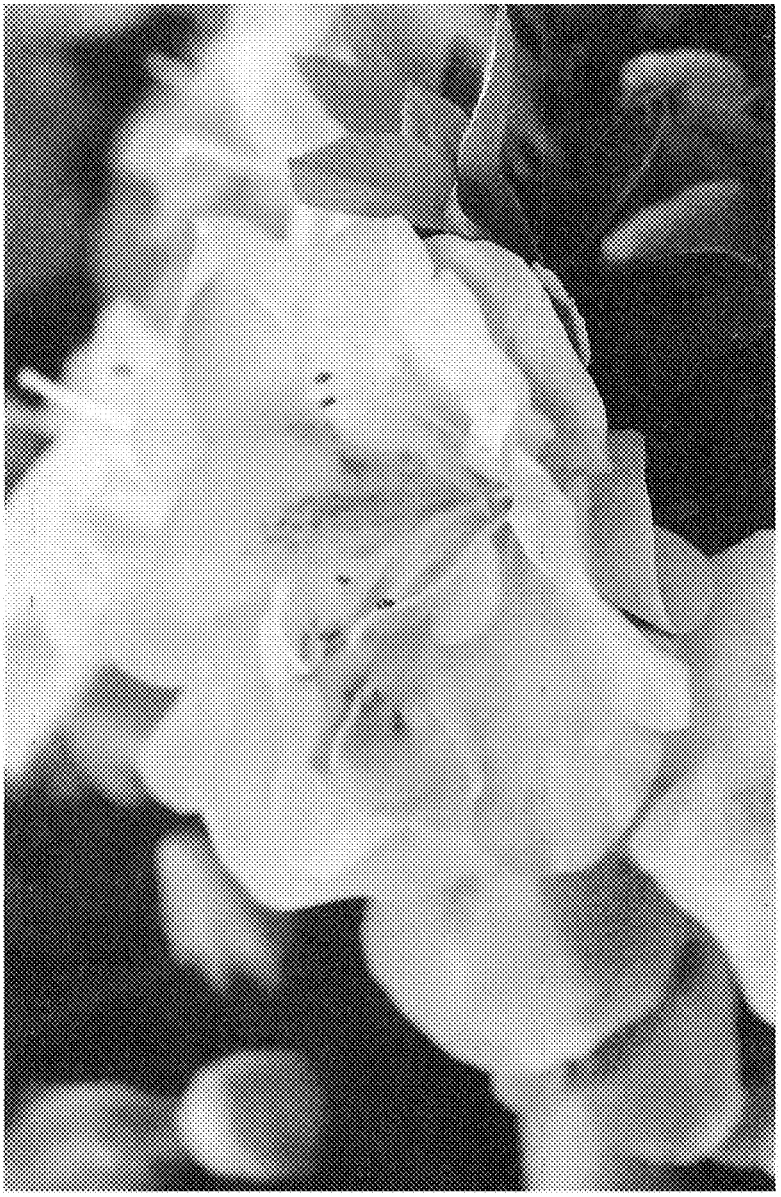

Latin name of the genus and species: *Rhododendron* hybrid.

Variety denomination: The inventive hybrid was selected from seedlings derived from a controlled cross between evergreen azaleas 'Susan Oliver' (female, unpatented hybrid) and 'H2009-273-028' (male, unpatented experimental hybrid). Prior to the designation of the varietal denomination, 'NCRX11' was referred to by its experimental code: 'H2012-243-042'.

BACKGROUND OF THE INVENTION

The present invention comprises a new and distinct hybrid evergreen azalea cultivar hereinafter referred to by the cultivar name 'NCRX11'. This hybrid azalea was developed by a controlled breeding program in Mills River, N.C. 'NCRX11' was selected for its double pink flowers, floriferousness, dense and prostrate growth habit, and consistent fall reblooming. It was selected from the controlled, hand pollination of emasculated female hybrid 'Susan Oliver' (unpatented) and male/pollen parent experimental hybrid H2009-273-028 (unpatented). The cross resulting in the new variety was conducted during the Spring of 2011. 'NCRX11' was first selected from this population of seedlings during the Summer of 2014.

Container trials were conducted using pine bark media supplemented with 1.04 kg·m-3 dolomitic lime, 0.74 kg·m-3 granulated micronutrients (ICL Specialty Fertilizers, Tel Aviv, Israel) and top-dressed with 5- to 6-month slow-release fertilizer (15-9-12, ICL Specialty Fertilizers). Full-sun field trials were conducted in plastic-covered, bark-amended clay soils with minimum winter temperatures of −2° F. (−19° C.) and maximum summer temperatures 98° F. (37° C.).

The first asexual propagation of 'NCRX11' occurred in 2015 by rooting stem cuttings at a research nursery in Mills River, N.C. 'NCRX11' roots readily from firm softwood cuttings treated with a basal dip of 3,000 ppm indole butyric acid (potassium salt) in water. 'NCRX11' has been found to retain its distinctive characteristics through successive asexual propagations over 5 years.

SUMMARY OF THE INVENTION

The following are the unique combination of characteristics of this new cultivar when grown under standard horticultural practices at a research nursery in Mills River, N.C.

1. Floriferous spring flower display.
2. Double pink flowers.
3. Prostrate, dwarf habit.
4. Consistent fall reblooming.

COMPARISON TO PARENT VARIETIES

'NCRX11' is similar in most horticultural characteristics to the seed parent. Plants of the new cultivar 'NCRX11' however differ in the following:

1. The new variety has pink flowers, while the seed parent has white flowers tinged with pink.
2. The new variety has double flowers, while the seed parent has semi-double flowers.

'NCRX11' is similar in most horticultural characteristics to the pollen parent. Plants of the new cultivar 'NCRX11' however differ in the following:

1. The new variety has a prostrate habit, while the pollen parent has a more upright, irregular habit.
2. The new variety has soft pink, double flowers, while the pollen parent has bright pink, single flowers.

COMMERCIAL COMPARISON

'NCRX11' can be compared to the commercial variety *Rhododendron* 'Roblec', U.S. Plant Pat. No. 15,339. Plants of the new cultivar 'NCRX11' are similar to plants of 'Roblec' in most horticultural characteristics. Plants of the new cultivar 'NCRX11', however, differ in the following:

1. Flower color of the new variety is RHS 65D, while the flower color of this comparator is RHS 73B.
2. Flowers of the new variety are double, while flowers of this comparator are semi-double.
3. Plants of the new variety are smaller than plants of this comparator.
4. The new variety has a prostrate habit, while this comparator has an upright habit.

'NCRX11' can be compared to the commercial variety *Rhododendron* 'NCRX3', U.S. Plant Pat. No. 32,819. Plants of the new cultivar 'NCRX11' are similar to plants of 'NCRX3' in most horticultural characteristics. Plants of the new cultivar 'NCRX11', however, differ in the following:

1. Plant habit of the new variety is prostrate, plant habit of 'NCRX3' is upwardly spreading. Plants of 'NCRX11' can be used as a groundcover; plants of 'NCRX3' are used as shrubs.
2. Perianth diameter of the new variety is on average 5 cm; perianth diameter of this comparator is on average 7 cm.
3. Plants of the new variety are at least 30% shorter than plants of this comparator.

BRIEF DESCRIPTION OF THE PHOTOGRAPHS

'NCRX11' is illustrated by the accompanying photographs, which show the plant's form, foliage, and inflorescences. The colors shown are as true as can be reasonably obtained by conventional photographic procedures. Colors in the photographs may differ slightly from the color values cited in the detailed botanical description, which accurately describe the new hybrid *Rhododendron.*

FIG. 1 Image showing a close-up of pink double flowers of 'NCRX11' in 3-gallon container; image taken from 3-year-old container plants grown in Grand Haven, Mich., in 2020.

Figure 2:
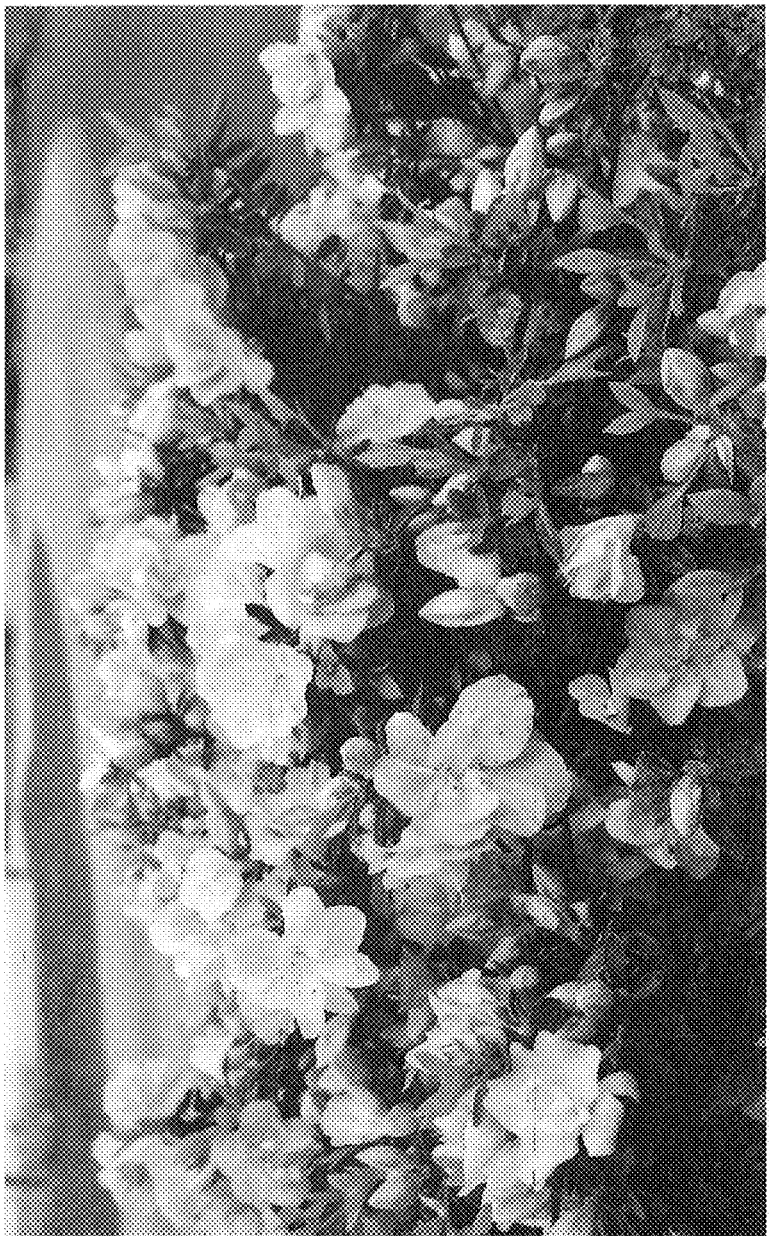

FIG. 2 Image showing floriferousness and habit of 'NCRX11' in a landscape setting in Grand Haven, Mich., in 2020.

DETAILED BOTANICAL DESCRIPTION

The following is a detailed description of the botanical characteristics of the new and distinct hybrid evergreen azalea known by the denomination 'NCRX11'. The detailed description was taken on a 3-year-old container-grown plant in Mills River, N.C., in 2021. Where pertinent, descriptive data was supplemented by observations/measurements taken on a 5-year-old individual located in field trials in Mills River, N.C., as well as information provided from cooperators in Grand Haven, Mich. All colors cited herein refer to The Royal Horticultural Society Colour Chart (The Royal Horticultural Society (R.H.S.), London, 2015 Edition. Where specific dimensions, sizes, colors, and other characteristics are given, it is to be understood that such characteristics are approximations or averages set forth as accurately as is practicable.

Botanical classification: *Rhododendron* hybrid 'NCRX11'.

PROPAGATION

Typical method: Softwood cuttings.

Root description: Dense, fibrous, freely branching, thin to medium texture. White to brown, not accurately measured with an R.H.S. chart.

Time to initiate rooting: 6 to 8 weeks.

Time to produce a rooted young plant: 12 to 16 weeks at 18 to 27° C.

PLANT

Plant type: Evergreen azalea.

Growth habit: Prostrate and dwarf.

Height: 30 to 60 cm.

Width: 60 to 75 cm.

Growth rate: Moderate.

Shoots (current year's growth):

*Length*.—Average 3.5 cm (range 1 to 6 cm).
*Diameter*.—About 0.2 cm.
*Color*.—Strong Yellow Green (RHS 145A).
*Texture*.—Pubescent.

Shoots (prior year's growth):

*Length*.—Average 6.2 cm. (range 3 to 9 cm.).
*Diameter*.—About 0.2 cm.
*Color*.—Moderate Brown (RHS 165A).
*Texture*.—Sparsely pubescent.

Branches (woody branches 2-4 years old):

*Length*.—About 11 cm.
*Diameter*.—About 0.6.
*Color*.—Moderate Brown (RHS 165A).
*Texture*.—Glabrous.

Internode length: Average 1.2 cm (0.5 to 2.5 cm).

FOLIAGE

Leaf:

*Type*.—Simple, evergreen.
*Arrangement*.—Alternate.
*Shape*.—Ovate.
*Apex*.—Mucronate.
*Base*.—Cuneate.
*Margin*.—Entire, ciliate.
*Venation*.—Reticulate.

Emerging leaf:

*Color*.—Upper surface: Strong Yellow Green (RHS 144A). Lower surface: Strong Yellow Green (RHS 144A).
*Texture*.—Upper surface: Pubescent. Lower surface: Pubescent.

Mature leaf:

*Length*.—About 2.5 cm.
*Width*.—About 1 cm.
*Color*.—Upper surface: Greyish Olive Green (RHS NN137A). Lower surface: Moderate Yellowish Green (RHS N138B).
*Texture*.—Sparsely pubescent.

Fall/winter leaf:
*Color*.—Upper surface: Light Olive (RHS 152B). Lower surface: Light Greyish Olive (RHS 195A).
Leaf attachment: Petiolate.
Petiole:
*Length*.—About 0.5 cm.
*Diameter*.—About 0.1 cm.
*Color*.—Moderate Yellow Green (RHS 147C).
*Texture*.—Pubescent.

FLOWER

Inflorescence:
*Type*.—Congested terminal raceme (truss).
*Flowering season*.—Mid-spring (mid-April-early May into June) reblooms in early fall (late September through October).
*Flowering habit*.—Free-flowering.
*Flower number*.—1-5 flowers per truss.
*Consistency in display*.—Blooms reliably in the spring and consistently reblooms in the fall.
*Lastingness of flowers*.—Each flower lasts approximately 3-7 days.
*Fragrance*.—None.
*Self-cleaning or persistent*.—Self-cleaning.
Truss bud:
*Length*.—About 1 to 1.5 cm.
*Diameter*.—About 0.5 to 0.8 cm.
Bud scales:
*Number*.—4 to 6.
*Length*.—About 0.8 to 1.2 cm.
*Width*.—About 0.5 to 1 cm.
*Color*.—Light Yellow Green (RHS 145B).
*Texture*.—Upper side is glabrous; lower side is pubescent at tip.
Emerging flowers:
*Shape*.—Elliptic, acuminate.
*Length*.—2.5 to 3.5 cm.
*Diameter*.—1.1 to 2 cm.
*Color*.—Strong Purplish Pink (RHS 62A).
*Texture*.—Glabrous.
Perianth:
*Shape*.—Funnel-shaped.
*Depth*.—About 2.5 to 3.5 cm.
*Diameter at anthesis*.—About 5 cm.
*Arrangement*.—Whorled.
*Aspect*.—Facing upwards and outwards.
*Attachment*.—Pedicellate.
Petals:
*Outer petals*.—Number: 9 to 11. Length: About 3 cm. Width: About 3 cm. Shape: Obovate. Apex: Obtuse. Base: Fused. Margin: Entire. Color: Color is consistent from opening to anthesis. Upper: Pale Purplish Pink (RHS 65D). Lower: Pale Purplish Pink (RHS 65D). Texture: Glabrous.
*Inner petals*.—Number: Average range 5 to 7. Length: About 2 cm. Width: About 1.8 cm. Shape: Obovate. Apex: Obtuse. Base: Fused. Margin: Entire. Texture: Glabrous. Color: Color is consistent from opening to anthesis. Upper: Near RHS Red-Purple 65D, base and center flushed White N155C. Lower: Near RHS Red-Purple 65D, base flushed White N155C.
Sepals:
*Number*.—5.
*Length*.—0.3 to 0.5 cm.
*Width*.—About 0.1 cm.
*Shape*.—Lanceolate.
*Apex*.—Cuneate.
*Margin*.—Ciliate.
*Color*.—Strong Yellow Green (RHS 145A).
*Texture*.—Pubescent.
Pedicels:
*Shape*.—Rounded.
*Length*.—About 1 cm.
*Diameter*.—About 0.15 cm.
*Color*.—Strong Yellow Green (RHS 145A).
*Texture*.—Pubescent.

REPRODUCTIVE ORGANS

Gynoecium:
*Pistil number*.—0 to 1.
*Pistil length*.—About 1.7 cm.
*Stigma shape*.—Orbicular.
*Stigma length*.—About 0.2 cm.
*Stigma width*.—About 0.1 cm.
*Stigma color*.—Pale Yellow Green (RHS 157A).
*Style length*.—About 1.6 cm.
*Style diameter*.—Less than 0.1 cm.
*Style color*.—White (RHS N155D).
*Ovary shape*.—Dome-shaped.
*Ovary length*.—About 0.5 cm.
*Ovary diameter*.—About 0.3 cm.
*Ovary color*.—Strong Yellow Green (RHS 145A).
*Texture*.—Pubescent.
Androecium:
*Stamen number*.—0 to 5.
*Anther shape*.—Ovoid with two apical pores.
*Anther attachment*.—Dorsifixed.
*Anther length*.—Less than 0.1 cm.
*Anther width*.—Less than 0.1 cm.
*Anther color*.—Dark Red (RHS 183A).
*Filament length*.—About 2 cm.
*Filament diameter*.—Less than 0.1 cm.
*Filament color*.—Pale Purplish Pink (RHS 65D).
*Amount of pollen*.—Normal.
*Pollen type*.—Thread-like.
*Pollen color*.—Greenish White (RHS NN155C).

OTHER CHARACTERISTICS

Fruit:
*Type*.—Capsule.
*Length*.—About 0.6 to 1.0 cm if successfully pollinated, about 0.4 cm if not.
*Diameter*.—About 0.5 to 1.0 cm if successfully pollinated, about 0.4 cm if not.
*Color*.—Immature fruit color: Strong Yellow Green (RHS 145A). Mature fruit color: Moderate Brown (RHS 200D).
*Texture*.—Pubescent.
Seed:
*Number*.—0 to hundreds per capsule.
*Length*.—Approximately 0.1 cm.
*Diameter*.—Less than 0.1 cm.
*Color*.—Moderate Orange Yellow (RHS 164B).
*Texture*.—Glabrous.
Disease and pest resistance: Not observed to be susceptible nor resistant to normal diseases and pests of *Rhododendron*.
Temperature tolerance: Has been reliably cold hardy in USDA 6B.

What is claimed is:

1. A new and distinct cultivar of *Rhododendron* plant named 'NCRX11' as herein illustrated and described.

* * * * *